United States Patent
O'Connell et al.

(10) Patent No.: US 10,524,904 B2
(45) Date of Patent: Jan. 7, 2020

(54) VALVE POSITIONING DEVICE

(71) Applicant: Medtronic, Inc., Minneapolis, MN (US)

(72) Inventors: Barry O'Connell, Ballybrit (IE); Declan P. Costello, Ballybrit (IE); Michael A. Colson, Mounds View, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 143 days.

(21) Appl. No.: 13/939,638

(22) Filed: Jul. 11, 2013

(65) Prior Publication Data
US 2015/0018944 A1    Jan. 15, 2015

(51) Int. Cl.
*A61F 2/24* (2006.01)
*A61B 90/00* (2016.01)

(52) U.S. Cl.
CPC ............ *A61F 2/2427* (2013.01); *A61B 90/39* (2016.02); *A61F 2/2418* (2013.01); *A61F 2230/0013* (2013.01); *A61F 2250/0098* (2013.01)

(58) Field of Classification Search
CPC .. A61F 2/24; A61F 2/2409; A61F 2250/0096; A61F 2250/0097; A61F 2250/0098; A61F 2/2418; A61F 2250/0036
USPC ....................................................... 623/1.34
See application file for complete search history.

(56) References Cited

U.S. PATENT DOCUMENTS

| | | | |
|---|---|---|---|
| 6,629,534 B1 | 10/2003 | St. Goar et al. | |
| 7,806,917 B2 * | 10/2010 | Xiao | 623/1.13 |
| 2004/0003819 A1 | 1/2004 | St. Goar et al. | |
| 2004/0127982 A1 * | 7/2004 | Machold et al. | A61F 2/2418 623/2.17 |
| 2004/0167619 A1 * | 8/2004 | Case | A61F 2/2418 623/1.34 |
| 2006/0235505 A1 * | 10/2006 | Oepen | A61F 2/915 623/1.15 |
| 2007/0088431 A1 | 4/2007 | Bourang et al. | |

(Continued)

FOREIGN PATENT DOCUMENTS

WO    20150196152 A1    12/2015

OTHER PUBLICATIONS

PCT/US2014/045293, PCT International Search Report and Written Opinion, dated Nov. 5, 2014.

(Continued)

*Primary Examiner* — Brian E Pellegrino
(74) *Attorney, Agent, or Firm* — Medler Ferro Woodhouse & Mills PLLC

(57) ABSTRACT

Medical devices for positioning a valve in a subject's body, such as a prosthetic heart valve in a subject's heart, are disclosed. The prosthetic heart valve may include a valve assembly, a frame, and a control arm. The prosthetic heart valve may include a commissural post or multiple commissural posts. The prosthetic heart valve may include a positional marker on a control arm. The prosthetic heart valve may include multiple positional markers on one or more control arms. The positional markers can be shapes, characters, or other symbols. The positional markers may themselves be asymmetric. The positional markers may be placed in an asymmetric location on a control arm. The control arm may be asymmetrically shaped.

20 Claims, 14 Drawing Sheets

(56) References Cited

U.S. PATENT DOCUMENTS

| | | |
|---|---|---|
| 2007/0093887 A1 | 4/2007 | Case et al. |
| 2008/0009746 A1 | 1/2008 | Forster et al. |
| 2009/0222082 A1 | 9/2009 | Lock et al. |
| 2010/0016943 A1* | 1/2010 | Chobotov ................ A61F 2/07 623/1.13 |
| 2010/0121436 A1 | 5/2010 | Tuval et al. |
| 2011/0022157 A1 | 1/2011 | Essinger et al. |
| 2011/0208297 A1 | 8/2011 | Tuval et al. |
| 2011/0264200 A1 | 10/2011 | Tran et al. |
| 2011/0319989 A1* | 12/2011 | Lane et al. .................. 623/2.11 |
| 2012/0078360 A1 | 3/2012 | Rafiee et al. |
| 2015/0366664 A1* | 12/2015 | Guttenberg ........... A61F 2/2418 623/2.17 |

OTHER PUBLICATIONS

EPC communication dated Dec. 12, 2018 in corresponding EP Appln.No. 14742435.2.

\* cited by examiner

VALVE POSITIONING DEVICE

BACKGROUND

In many medical procedures, a device is inserted temporarily or permanently into a patient. One example includes prosthetic heart valves. Heart valves have been developed that can be inserted via a minimally invasive procedure. Often procedures are performed via a catheter-based delivery system, with the heart valve collapsed on the catheter inserted into the patient, and the heart valve is then expanded when correctly positioned in the patient. The heart valve must be properly positioned before final deployment in the patient.

Existing catheter-based methods prevent certain visualization techniques from being used. Correct positioning of a heart valve prosthesis relative to a native heart valve can be achieved by using radiographic images, including fluoroscopy in some cases. Certain radiographic images are two dimensional and do not indicate depth. More importantly, certain radiographic images do not provide an easily identifiable device to distinguish whether the heart valve prosthesis is correctly positioned and do not provide a device to distinguish how the device is oriented without further investigation. Incorrect positioning of a heart valve prosthesis can lead to patient complications. Physicians interpret the radiographic image and adjust the position of the prosthetic heart valve as needed. Physicians thus need a device that can help in quickly and accurately positioning the heart valve prosthesis relative to the native heart valve and directly illustrate how the heart valve prosthesis is currently oriented.

BRIEF SUMMARY

In accordance with some embodiments, a prosthetic heart valve is disclosed. This heart valve prosthesis includes a valve assembly, a frame, and a control arm. The frame may include commissural posts. The control arm, also known as an engagement arm, may include a positional marker. The positional marker is positioned on a control arm of the prosthetic heart valve. The prosthetic heart valve may have one, two, or more control arms. The positional marker can be a symbol, shape, character, letter, or any other indicator. The positional marker may be made of a material with a different radiopacity than other portions of the prosthetic heart valve. The prosthetic heart valve may include a positional marker on one control arm, a positional marker on two control arms, or a positional marker on more than two control arms. The prosthetic heart valve may include multiple positional markers on one, two, or more control arms.

The positional marker may be asymmetric. The positional marker may be positioned closer to a first commissural post than a second commissural post. The control arm may also be asymmetric separate from or in conjunction with an asymmetric positional marker. The positional marker may provide a means to orient the prosthetic heart valve with a native heart valve. The positional marker may provide a means to orient the prosthetic heart valve with a native heart valve in conjunction with other elements of the heart valve.

In some embodiments a prosthetic heart valve comprises a biological valve assembly, a frame coupled to the biological valve assembly, the frame comprising a first commissural post, a second commissural post, and a control arm attached to the first commissural post and the second commissural post.

In some embodiments the control arm forms a shape between the commissural posts. In some embodiments the control arm further comprises a positional marker.

In some embodiments the control arm forms a symmetric shape between the first commissural post and the second commissural post. In some embodiments the positional marker is positioned on the control arm closer to one commissural post than another commissural post.

In some embodiments the positional marker comprises a bend in the control arm.

In some embodiments the positional marker comprises multiple bends in the control arm.

In some embodiments the positional marker comprises a geometric shape.

In some embodiments the positional marker comprises a character.

In some embodiments the positional marker comprises an asymmetric character.

In some embodiments the positional marker comprises an asymmetric shape.

In some embodiments the frame comprises a first material with a first radiopacity, and wherein the positional marker comprises a second material with a second radiopacity.

In some embodiments the commissural posts comprise a first material with a first radiopacity, and wherein the positional marker comprises a second material with a second radiopacity.

In some embodiments the prosthetic heart valve comprises the positional marker welded to the control arm.

In some embodiments the shape of the control arm between the commissural posts is asymmetric.

In some embodiments the assembly further comprises a second control arm, and wherein the shape of each control arm is asymmetric.

In some embodiments the shape of each control arm differs from all other control arms.

Some embodiments provide a method of implanting a prosthetic heart valve, the method comprising placing a prosthetic heart valve at least partially in a heart of a subject. In some embodiments the prosthetic heart valve comprises a valve assembly, a frame, and two or more commissural posts coupled to the frame, the posts being arranged circumferentially around a central longitudinal axis of the valve assembly, and the frame is configured to assume a collapsed state and an expanded state, and a control arm attached to two different commissural posts, and the control arm having a positional marker.

In some embodiments placing the prosthetic heart valve in a heart of a subject comprises placing the prosthetic heart valve in a vicinity of a native heart valve having native commissures, while the commissural posts are in the collapsed state. In some embodiments the method comprises generating a fluoroscopic image of the native commissures and the prosthetic heart valve. In some embodiments the method comprises determining whether one post of the prosthetic heart valve is aligned with one native commissure and determining the position of the positional marker relative to the native heart valve. In some embodiments the method comprises rotating the prosthetic heart valve to correct a rotational alignment of the prosthetic heart valve with the native commissure.

In some embodiments the posts are in the expanded state after the prosthetic heart valve is rotated.

In some embodiments the prosthetic heart valve comprises multiple control arms, and wherein each control arm includes a positional marker.

In some embodiments the method further comprises that verifying the prosthetic heart valve is rotationally aligned after rotating the valve assembly.

In some embodiments prosthetic heart valve comprises a valve assembly, a frame coupled to the valve assembly, the frame comprises a first commissural post, a second commissural post, a control arm attached to two commissural posts. In some embodiments the control arm forms a symmetric arc between the commissural posts. In some embodiments the control arm comprises a positional indicator.

In some embodiments the positional indicator comprises a radiographic marker.

In some embodiments the positional indicator is asymmetric.

The embodiments and related concepts will be more fully understood from the following detailed description of the embodiments thereof.

DETAILED DESCRIPTION OF EMBODIMENTS

While the disclosure refers to illustrative embodiments for particular embodiments, it should be understood that the disclosure is not limited thereto. Modifications can be made to the embodiments described herein without departing from the spirit and scope of the present disclosure. Those skilled in the art with access to this disclosure will recognize additional modifications, embodiments, and embodiments within the scope of this disclosure and additional fields, in which the disclosed examples could be applied. Therefore, the following detailed description is not meant to be limiting. Further, it is understood that the apparatus and methods described below can be implemented in many different embodiments of hardware. Any actual hardware described is not meant to be limiting. The operation and behavior of the apparatus and methods presented are described with the understanding that modifications and variations of the embodiments are possible.

References to "one embodiment," "an embodiment," "some embodiments," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1:
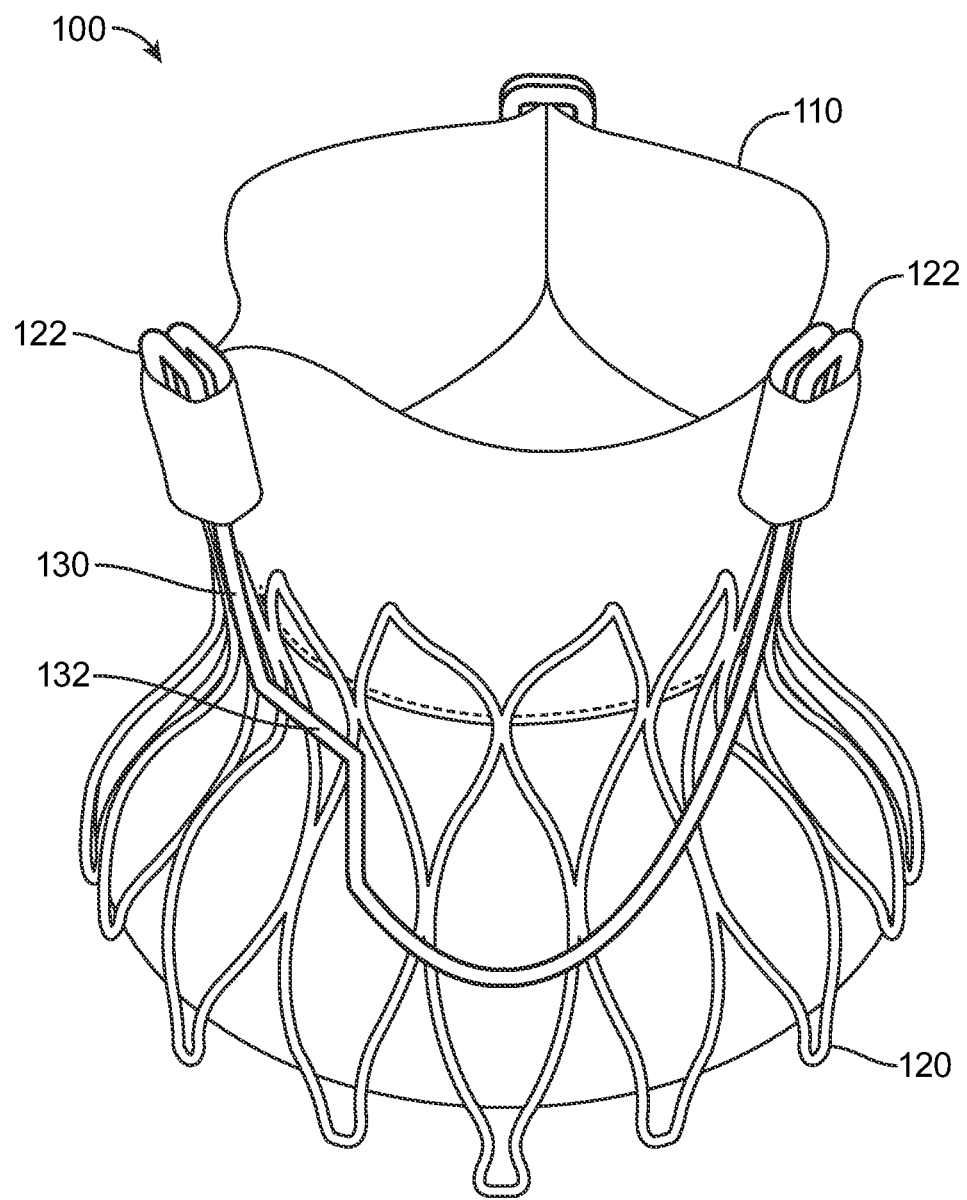
FIGS. 1-5 illustrate a prosthetic heart valve including a positional marker in accordance with some embodiments.

Reference is now made to FIG. 1 that includes a schematic illustration of a prosthetic heart valve 100. In some embodiments, the prosthetic heart valve 100 may include a valve assembly 110 and a frame 120. In some embodiments the frame 120 may comprise commissural posts 122. In some embodiments there may be one, two, three, or more commissural posts 122 comprising the frame 120 of the prosthetic heart valve 100. In some embodiments the frame 120 has multiple sections and those sections are arranged in a cylindrical shape. This cylindrical shape may be expanded or compressed in certain areas as necessary or desired for valve positioning or implantation.

The valve assembly 110 may comprise any biocompatible material. The valve assembly 110 may comprise any biological material. For example valve assembly 110 may comprise bovine, porcine, or equine tissue, such as valve tissue or pericardium. The valve assembly 110 may comprise any natural tissue. Valve assembly 110 may comprise multiple pieces stitched, joined, attached or otherwise coupled to each other.

In some embodiments the frame 120 has multiple sections and those sections are arranged along a longitudinal axis. The frame 120 may be comprised of any suitable material, for example nitinol or stainless steel.

In addition to having commissural posts 122, the prosthetic heart valve 100 may also include a control arm 130. In some embodiments, the prosthetic heart valve 100 may include one, two, three, or more control arms 130. Control arms 130 can extend from one commissural post 122 to another in various shapes including an arc, a line, or various other shapes. The shapes of the control arms 130 can also vary so that each prosthetic heart valve 100 having two or more control arms 130 may include control arms 130 of different shapes. The control arms 130 may be comprised of any suitable material, for example nitinol or stainless steel.

FIG. 1 illustrates one potential embodiment of a heart valve 100. FIG. 1 shows a prosthetic heart valve 100 comprising a valve assembly 110 and frame 120. In accordance with some embodiments, the frame 120 may include three commissural posts 122. In some embodiments the prosthetic heart valve 100 may include three control arms 130. In some embodiments one of the control arms 130 may include a positional marker 132. In some embodiments the positional marker 132 may comprise a bend in the control arm 130. In some embodiments the positional marker 132 may comprise multiple bends in the control arm 130. In some embodiments the control arm 130 comprises an arc shape that extends between the commissural posts 122 of the prosthetic heart valve 100.

In some embodiments the positional marker 132 can be positioned at various locations along the control arm 130. In some embodiments the positional marker 132 can be positioned symmetrically at the lowest point of the arc formed by control arm 130. In some embodiments the positional marker 132 can be positioned asymmetrically about the control arm 130. For example, positional marker 132 can be positioned above the lowest point of the arc formed by control arm 130.

In addition, positional marker 132 may comprise a material with a different radiopacity than other portions of the prosthetic heart valve 100. In some embodiments, the positional marker 132 may have different radiopacity from the control arm 130. In some embodiments, the positional marker 132 may have different radiopacity from the frame 120. In some embodiments, the positional marker 132 may have different radiopacity from the commissural posts 122. In some embodiments, the positional marker 132 may have different radiopacity from all other portions of the prosthetic heart valve 100.

Figure 2:
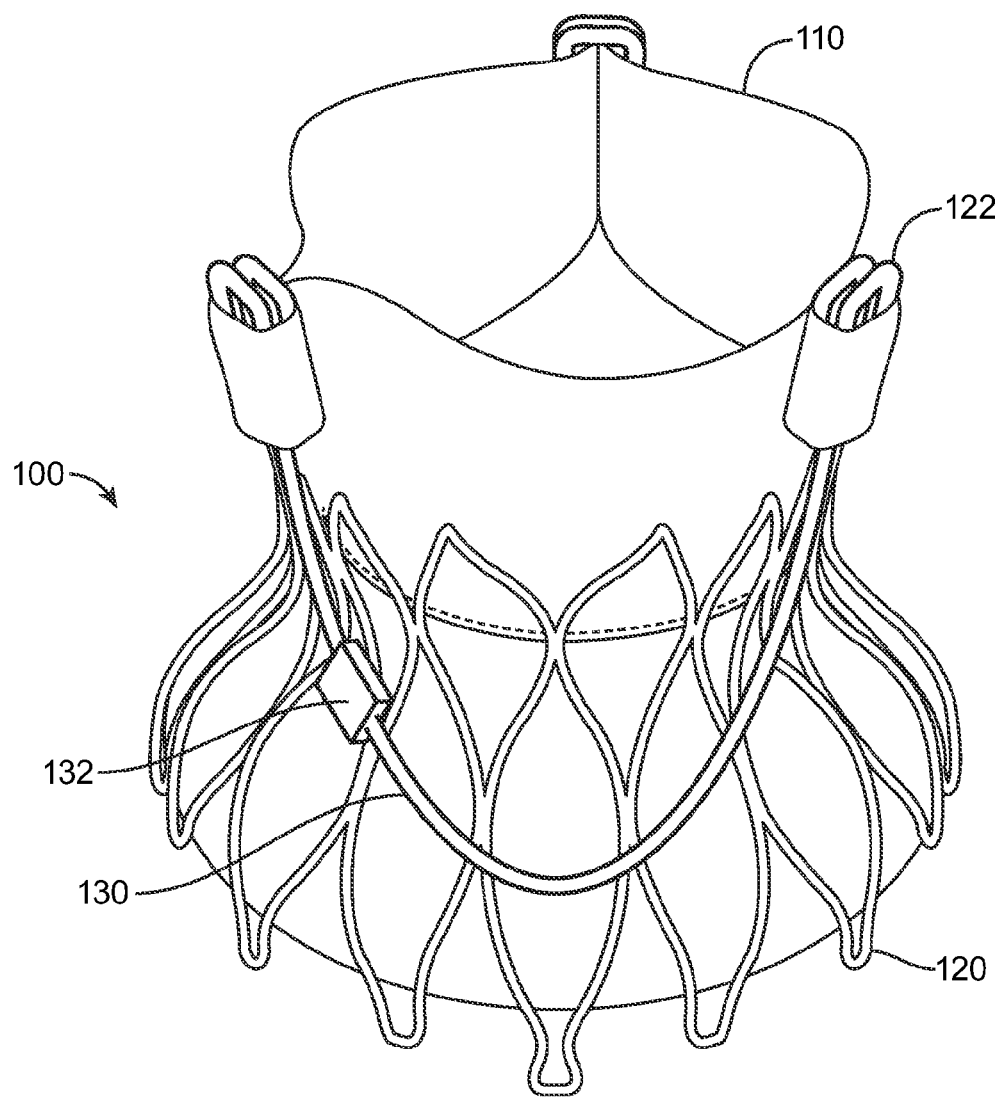

FIG. 2 illustrates a prosthetic heart valve 100 including a valve assembly 110, frame 120, and commissural posts 122. FIG. 2 illustrates an embodiment with three commissural posts 122 and three control arms 130. FIG. 2 illustrates an embodiment where a control arm 130 includes a positional marker 132 identified by a geometric shape. The shape may include a square, circle, oval, triangle, rectangle, or any other geometric shape. In addition, FIG. 2 illustrates that the positional marker 132 is offset and asymmetrically positioned on the control arm 130. In FIG. 2 positional marker 132 is positioned off to the left side of the control arm 130 and is closer to one commissural post 122 than another commissural post 122. This provides an asymmetric shape of the control arm 130. In some embodiments the control arm 130 comprises a wire. In some embodiments the positional marker 132 comprises a bend in the wire of the control arm 130. In some embodiments the positional marker 132 comprises multiple bends in the wire of the control arm 130.

As shown, positional marker 132 is centered about the wire of control arm 130. However, positional marker 132 can be positioned interior to or exterior from the arc formed by control arm 130. In some embodiments, the positional marker 132 may comprise a bend in control arm 130.

In some embodiments, the positional marker 132 may comprise multiple bends in control arm 130. In some embodiments, bends may be toward the frame 120. In some embodiments, bends may be away from the frame 120. In some embodiments the positional marker 132 may be positioned on the side of control arm 130 closer to the frame 120. In some embodiments the positional marker 132 may be positioned on the side of control arm 130 away from the frame 120. In some embodiments the positioning of the positional marker 132 relative to the control arm 130 may provide added benefits. For example, when the positional marker 132 is positioned on the side of the control arm 130 toward the frame, the positional marker 132 may provide additional pressure on the native leaflets of the native heart valve 210 proximate the control arms 130. In addition, when the positional marker 132 is positioned on the side of the control arm 130 away the frame, the positional marker 132 may provide additional pressure on other portions of the native heart valve 210 proximate the control arms 130.

In some embodiments, the geometric shape can be rotated in any desirable configuration that may help to identify the configuration of the prosthetic heart valve 100. In addition to geometric shapes, other shapes as would be understood or contemplated by one of ordinary skill in the art could be used. In some embodiments, symbols, logos, initials or other identifying characteristics could be used.

Figure 3:
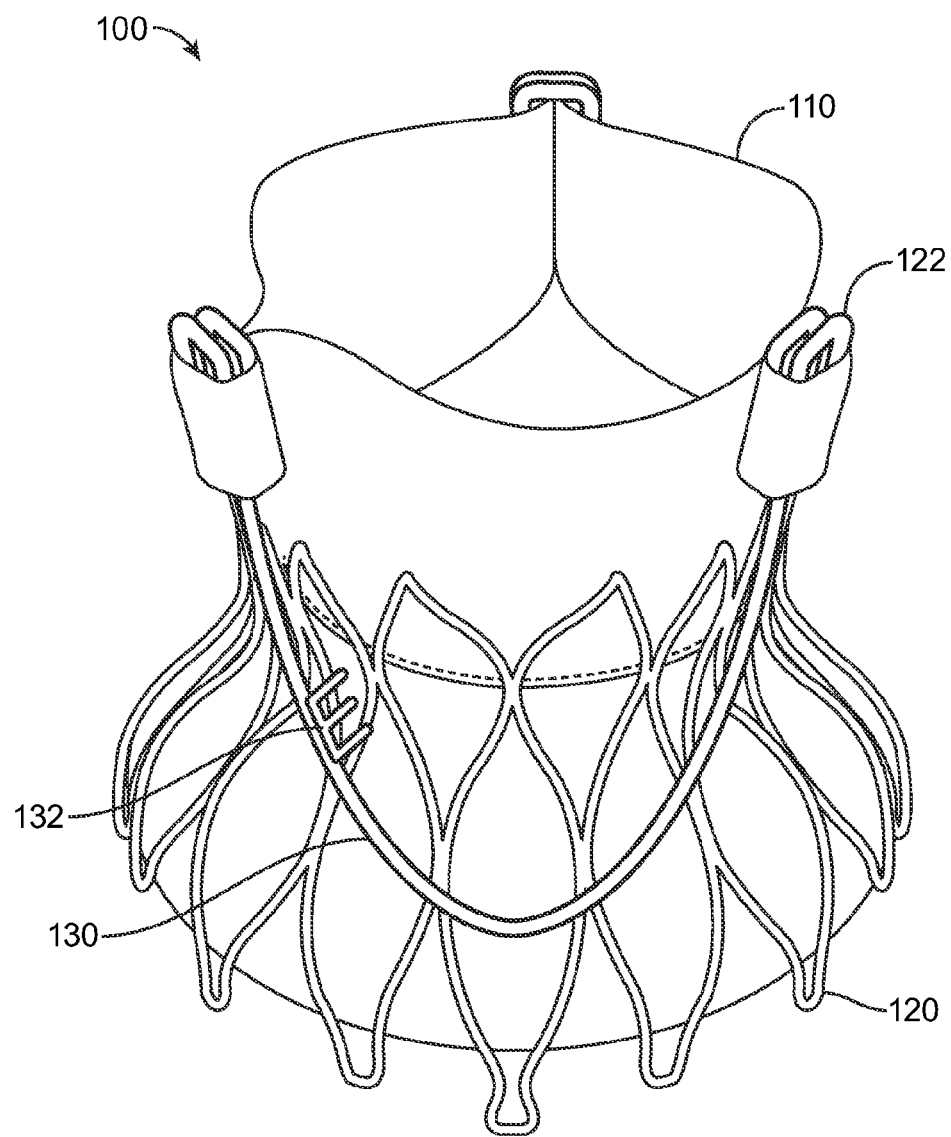

FIG. 3 illustrates a prosthetic heart valve 100 that includes a valve assembly 110, a frame 120, and control arms 130. In some embodiments, the frame 120, as shown in FIG. 3, may include multiple commissural posts 122. FIG. 3 illustrates an embodiment where the positional marker 132 comprises an asymmetric shape. In some embodiments this asymmetric shape may include an asymmetric character. In some embodiments this asymmetric shape may include an asymmetric letter.

In some embodiments this asymmetric shape may be positioned at multiple points on the control arm 130. In some embodiments the asymmetric shape of the positional marker 132 may be positioned closer to one commissural post 122 than another commissural post 122. This provides two levels of identification to examine whether the prosthetic heart valve 100 is positioned appropriately. By having the positional marker 132 comprise an asymmetric shape and having the positional marker 132 also asymmetrically positioned on the control arm 130 there are two checks to determine which way the heart valves is oriented.

In some embodiments the asymmetric shape can be positioned to reflect an easily identifiable orientation to aid in identifying the position of the prosthetic heart valve 100. The asymmetric shape can be positioned in any orientation. For example, in some embodiments the asymmetric shape of positional marker 132 may comprise a character. In some embodiments, the asymmetric shape of positional marker 132 may comprise a letter of an alphabet. In some embodiments, as shown in FIG. 3 the asymmetric shape of the positional marker 132 may comprise the letter "E." For example, the "E" as positioned on the control arm 130 may face such that the three extending portions of the capital "E" extend toward the center line of the prosthetic heart valve 100 as illustrated in FIG. 3. In some embodiments the three extending portions of the capital "E" may extend away from the center of the prosthetic heart valve 100 or outward.

In some embodiments when the positional marker 132 is used at certain positions of the control arm 130 the asymmetric shape can be positioned such that the three extending portions will extend upward toward valve assembly 110. In other embodiments the three extending prongs of the "E" or asymmetric shape which may comprise positional marker 132 may extend toward the bottom of the frame 120, away from valve assembly 110.

Figure 4:
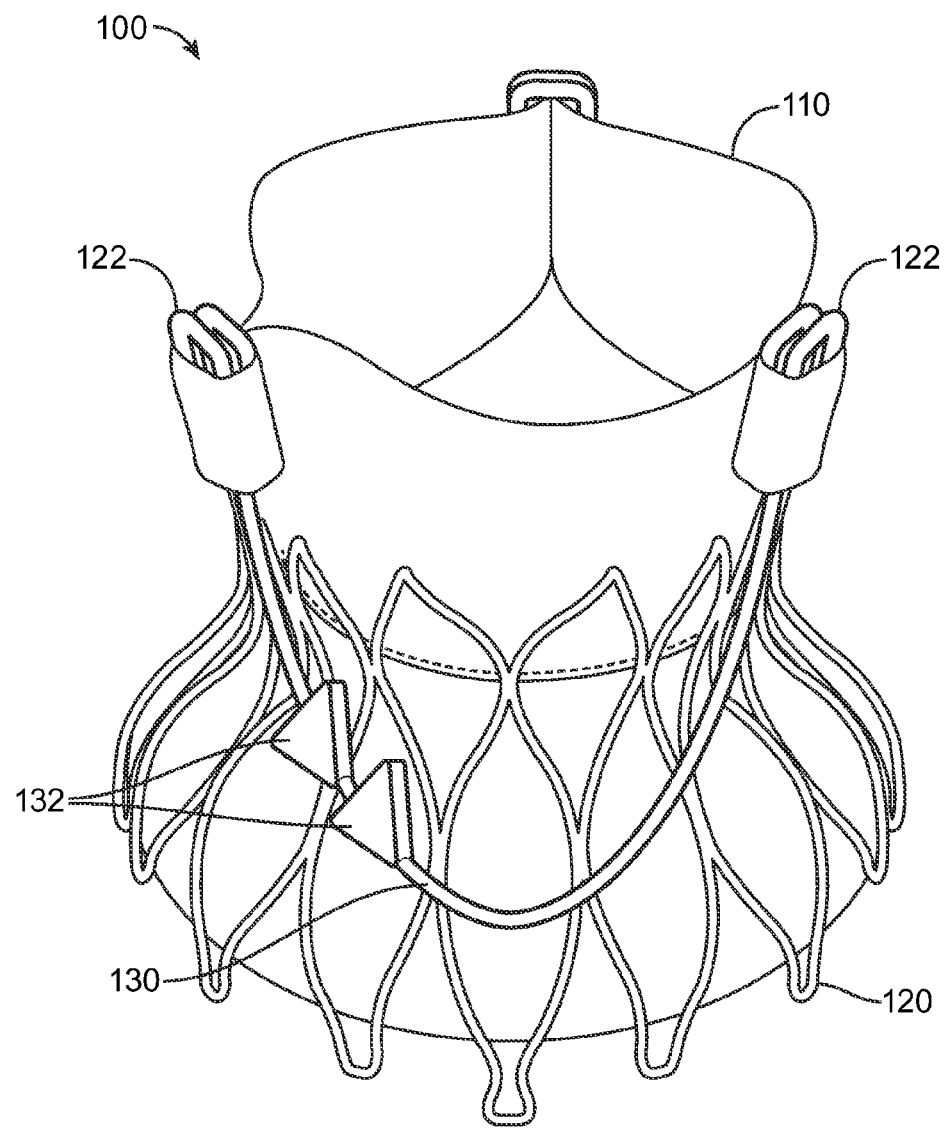

FIG. 4 illustrates a prosthetic heart valve 100 which may comprise a valve assembly 110, frame 120, and control arms 130. In addition the frame 120 may comprise commissural posts 122. FIG. 4 illustrates an embodiment where multiple positional markers 132 are used on a control arm 130. This embodiment illustrates using similar positional markers 132 both positioned on one portion of the control arm 130.

In some embodiments multiple positional markers 132 can be positioned closer to one commissural post 122 and farther away from another commissural post 122. In some embodiments using multiple positional markers 132 may provide an easier identifiable position of prosthetic heart valve 100 when a person examines the configuration of the prosthetic heart valve 100.

In some embodiments two different positional markers 132 could be used on the same control arm 130. In some embodiments a shape could be used and a different symbol could be used in conjunction with the shape. For example in some embodiments a triangle could be used as well as a character could be used on the same control arm 130.

In some embodiments the positional markers 132 can both be positioned to indicate, direct, or point in the same direction as shown in FIG. 4. In FIG. 4 the two positional markers 132 are embodied by triangles. In some embodiments the multiple positional markers 132 can indicate one direction or another. As shown in FIG. 4, the positional markers point away from the center of the prosthetic heart valve 100 in a two-dimensional image. In some embodiments the positional markers 132 can point away from the center. In some embodiments the positional markers 132 can point towards the center. In some embodiments the positional markers 132 can point upward. In some embodiments the positional markers 132 can point downward. In some embodiments the positional markers 132 can point in any direction.

Figure 5:
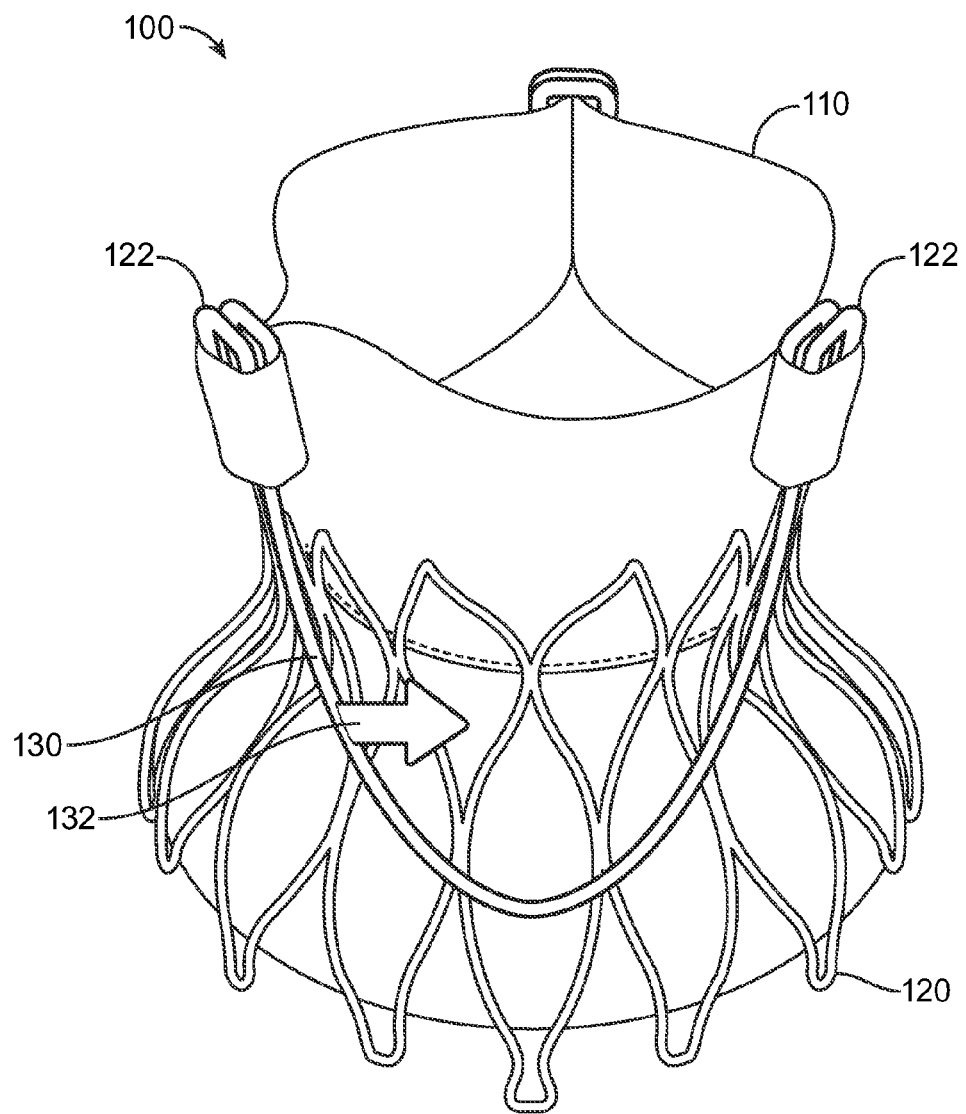

FIG. 5 illustrates a prosthetic heart valve 100 comprising a valve assembly 110, frame 120, and control arms 130. The frame 120 may include commissural posts 122. In some embodiments, as shown in FIG. 5, the positional marker may comprise a directional marker, such as an arrow. This arrow illustrates an asymmetric shape which can point, direct, indicate, or illustrate a certain direction of the valve when the valve is oriented in an appropriate matter. For example, if the valve is positioned such that the control arm 130 is proximate the viewer when an image is taken the arrow can point right, as illustrated in FIG. 5. Conversely, if the control arm 130 was positioned at the back of the image, or distal the viewer, the arrow would point or indicate left.

In some embodiments the positional markers 132 can be a separate element from control arms 130 where the positional markers 132 are appropriately attached to control arms 130. In some embodiments positional markers 132 can be coupled to a control arm 130. In some embodiments positional markers 132 may be welded to control arms 130. In some embodiments positional markers 132 may be molded or otherwise connected to a control arm 130. One of ordinary skill in the art will understand the multiplicity of ways positional markers 132 could be attached to control arms 130 if they were created as separate parts.

In addition, a control arm 130 and a positional marker 132 can be an integral part.

Positional markers 132 can be made of any suitable material that can be introduced into a subject. This would include, but is not limited to, metals, plastics, polymers, a biocompatible material, and any other suitable material known to a person of ordinary skill in the art.

Figure 6:
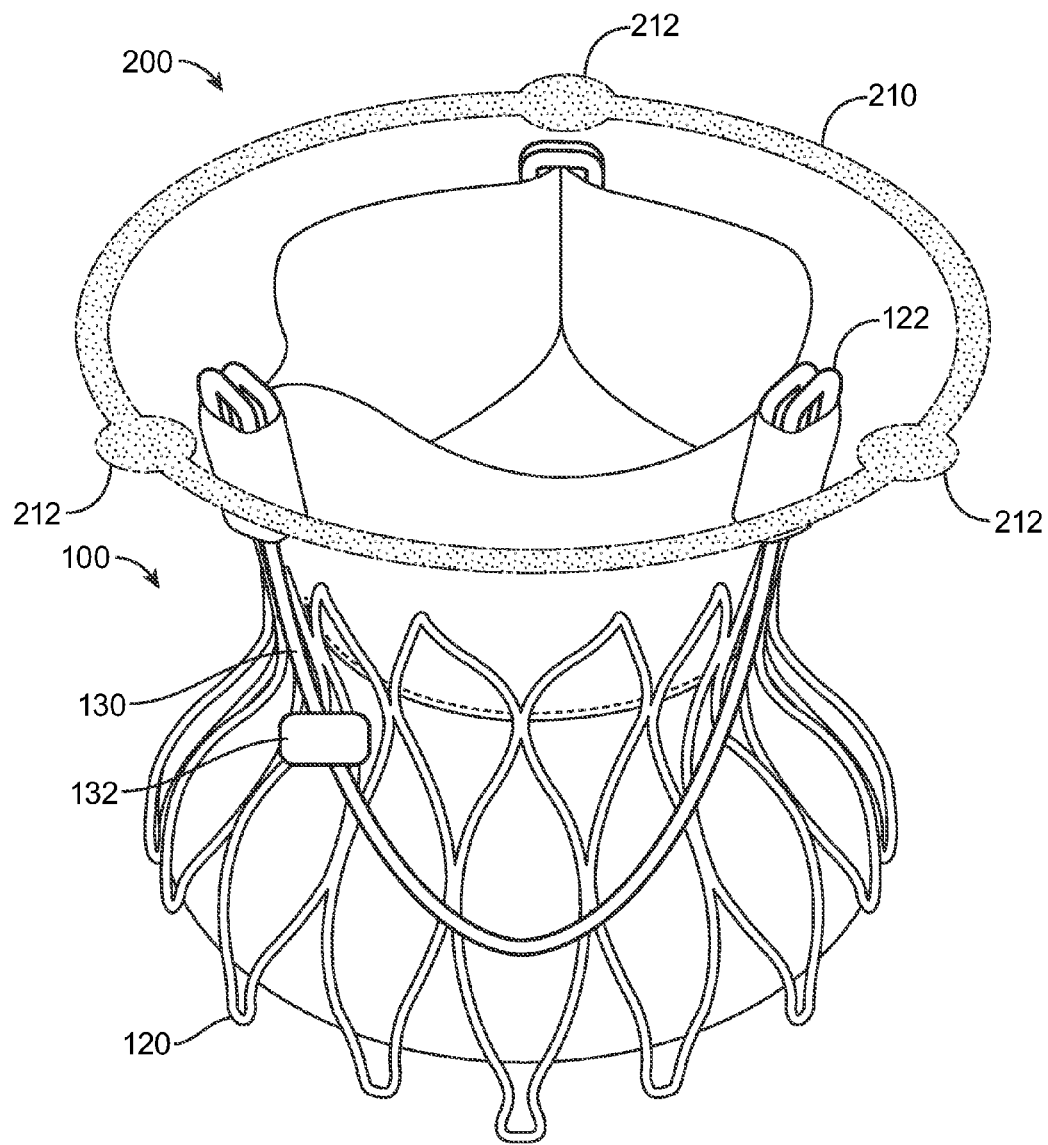
FIG. 6 illustrates a prosthetic heart valve being positioned relative to a native heart valve in accordance with some embodiments.

FIG. 6 illustrates another embodiment. In some embodiments the prosthetic heart valve 100 is at least partially placed in the subject's heart 200. The prosthetic heart valve 100 may comprise two commissural posts 122, a valve assembly 110, a frame 120, a control arm 130, and a positional marker 132. In some embodiments there may be three or more commissural posts 122. In some embodiments commissural posts 122 can be arranged around a central longitudinal axis of the prosthetic heart valve 100. In some embodiments the prosthetic heart valve 100 and its associated parts, including valve assembly 110, frame 120, commissural posts 122, control arm 130, and positional marker 132, are configured to assume a collapsed state. In some embodiments the prosthetic heart valve 100 is configured to assume an expanded state.

In some embodiments the prosthetic heart valve 100 includes three control arms 130. In some embodiments each control arm 130 is attached to two different commissural posts 122. Where prosthetic heart valve 100 includes multiple commissural posts 122 and multiple control arms 130, the prosthetic heart valve 100 may include one or more positional markers 132 on one control arm 130. In some embodiments two control arms 130 of prosthetic heart valve 100 may each include a positional marker 132. In some embodiments every control arm 130 may include a positional marker 132. In some embodiments each control arm 130 may include one or more positional markers 132.

In some embodiments the prosthetic heart valve 100 is placed in the subject's heart 200. In some embodiments placing the prosthetic heart valve 100 in the subject's heart 200 includes placing the valve in a vicinity of a native heart valve 210. In some embodiments the native heart valve 210 may include native commissures 212. In some embodiments positioning the prosthetic heart valve 100 relative to the native heart valves 210 is performed by aligning commissural posts 122 with native commissures 212. In some embodiments the prosthetic heart valve 100 is configured to collapse to a collapsed state. In some embodiments the prosthetic heart valve 100 is configured to expand to an expanded state.

In some embodiments the prosthetic heart valve 100 is positioned in the subject's heart 200 via a blood vessel. In some embodiments after the prosthetic heart valve 100 is positioned in the subject's heart 200, a radiographic or fluoroscopic image may be generated. In some embodiments the radiographic or fluoroscopic image may depict at least a portion of prosthetic heart valve 100 and at least a portion of the native heart valve 210. In some embodiments prosthetic heart valve 100 may be positioned relative to a portion of the native heart valve 210 based on the image. In some embodiments prosthetic heart valve 100 may be rotated relative to a portion of the native heart valve 210 based on the image.

In some embodiments prosthetic heart valve 100 may be aligned relative to a portion of the native heart valve 210 based on the image. In some embodiments the prosthetic heart valve 100 may be expanded to an expanded state or a partially expanded state while it is positioned, rotated, or aligned with a portion of native heart valve 210. In some embodiments the prosthetic heart valve 100 may be expanded to an expanded state after it is positioned, rotated, or aligned with a portion of native heart valve 210.

In some embodiments the configuration of the prosthetic heart valve 100 relative to the native heart valve 210 can be performed by examining the position of the control arms 130. In some embodiments the configuration of the prosthetic heart valve 100 relative to the native heart valve 210 can be performed by examining the position of the positional marker 132. In some embodiments, the positional marker 132 is asymmetrically placed on one control arm 130.

Figure 7A:
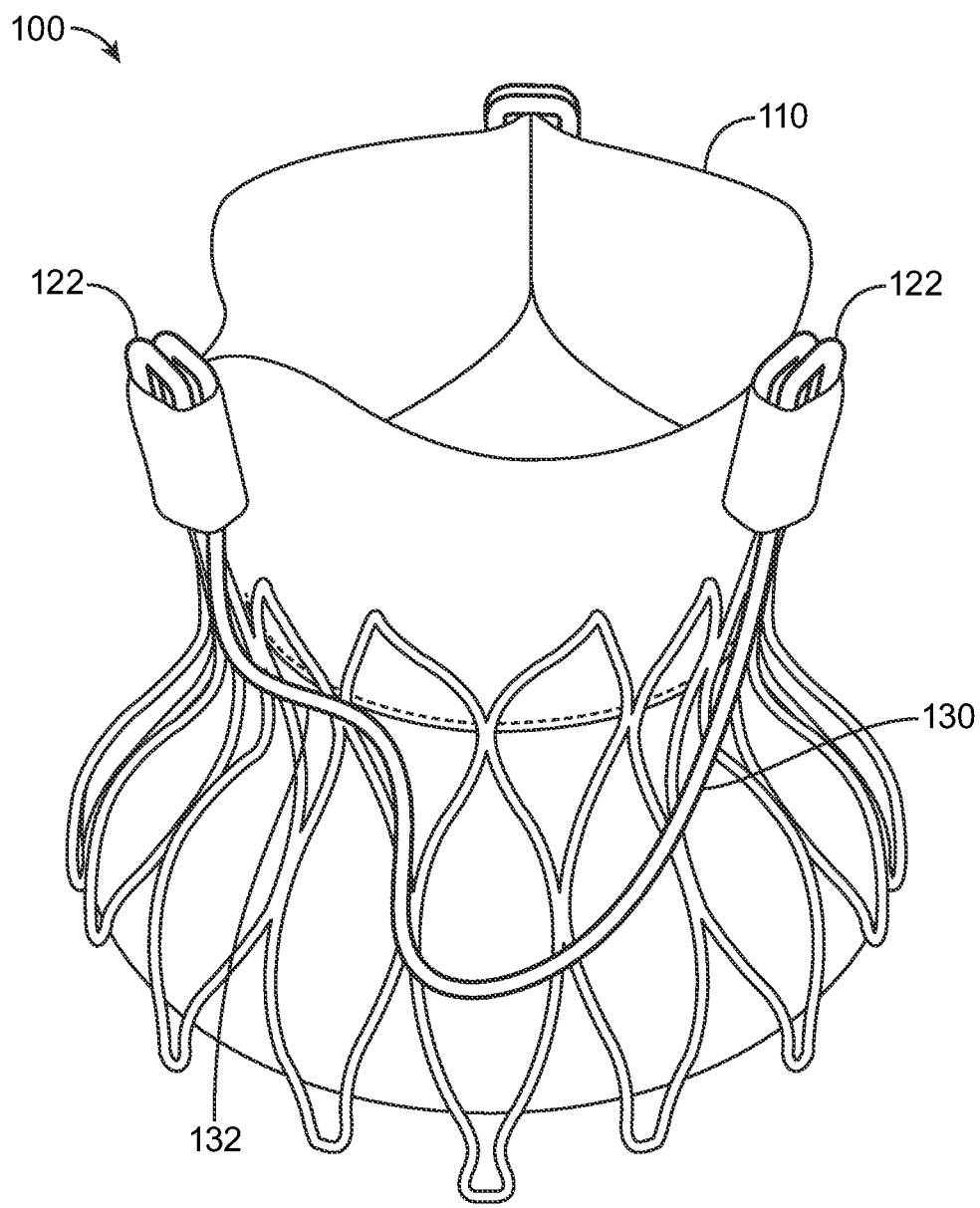
FIGS. 7a, 7b, and 8-10 illustrate a prosthetic heart valve including a positional marker in accordance with some embodiments.
Figure 7B:
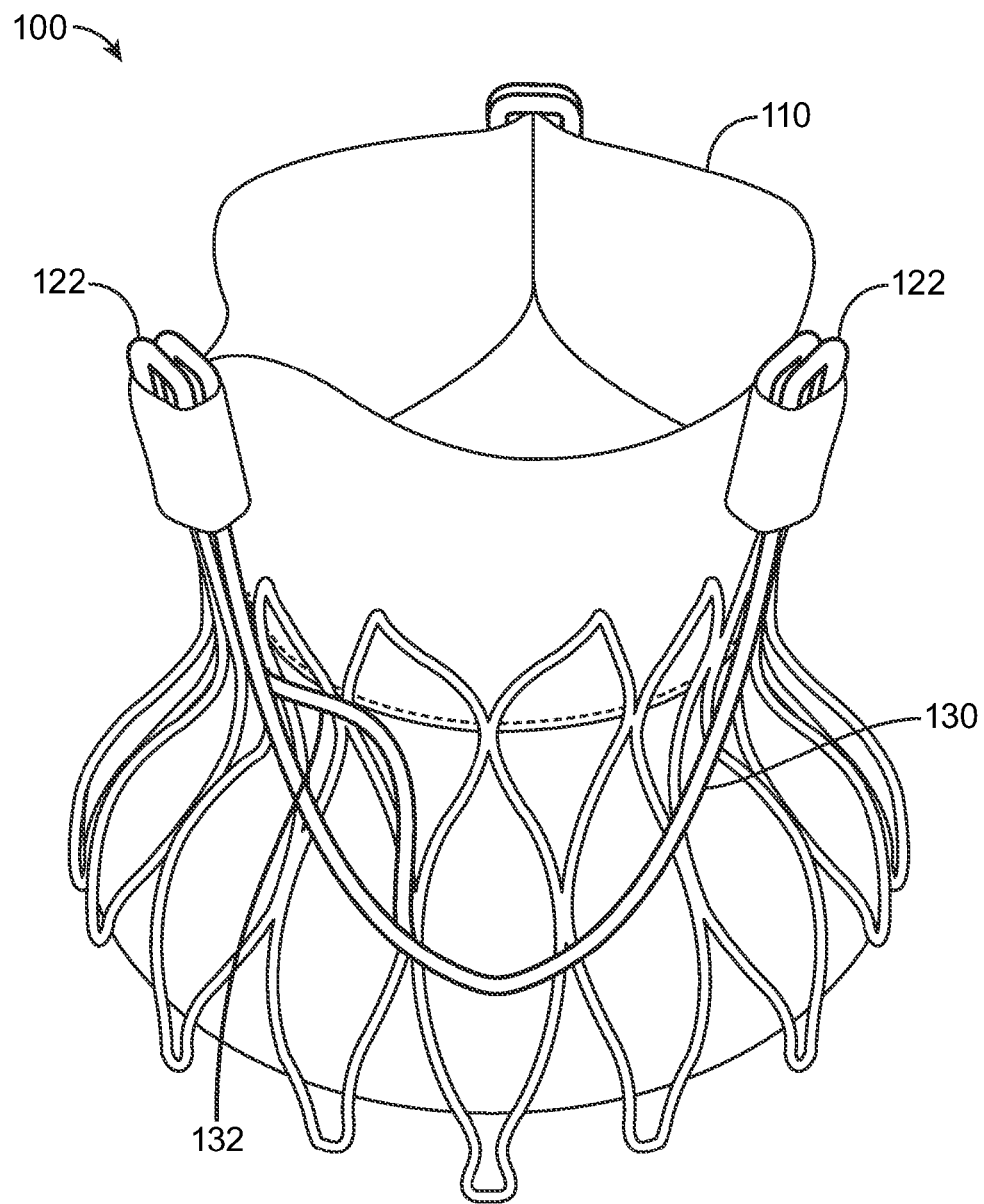

Prosthetic heart valve 100 may include a valve portion 110, frame 120, and two commissural posts 122, as shown in FIGS. 7a and 7b. In some embodiments the control arm 130 may be asymmetric. In some embodiments the control arm 130 may have straight bends making it asymmetric. In some embodiments the control arm 130 may have curved bends, as illustrated in FIGS. 7a and 7b. In some embodiments, the control arm 130 may have a straight and a curved bend or multiple straight and multiple curved bends. In some embodiments the asymmetric control arm 130 can be configured in such a way that one examining the configuration of prosthetic heart valve 100 will be able to quickly and easily determine how prosthetic heart valve 100 is oriented.

In some embodiments prosthetic heart valve 100 may include a valve portion 110, a frame 120, two commissural posts 122, and two or more control arms 130. In some embodiments each control arm 130 may include a different positional marker 132. In some embodiments the control arm 130 may serve as the positional marker 132.

In some embodiments each control arm 130 may be configured differently. In some embodiments each control arm 130 may be shaped differently such that one examining the orientation of prosthetic heart valve 100 can determine which control arm 130 is positioned relative to the person examining the prosthetic heart valve 100, the subject's heart 200, the native heart valve 210, and/or the native commissures 212.

Figure 8:
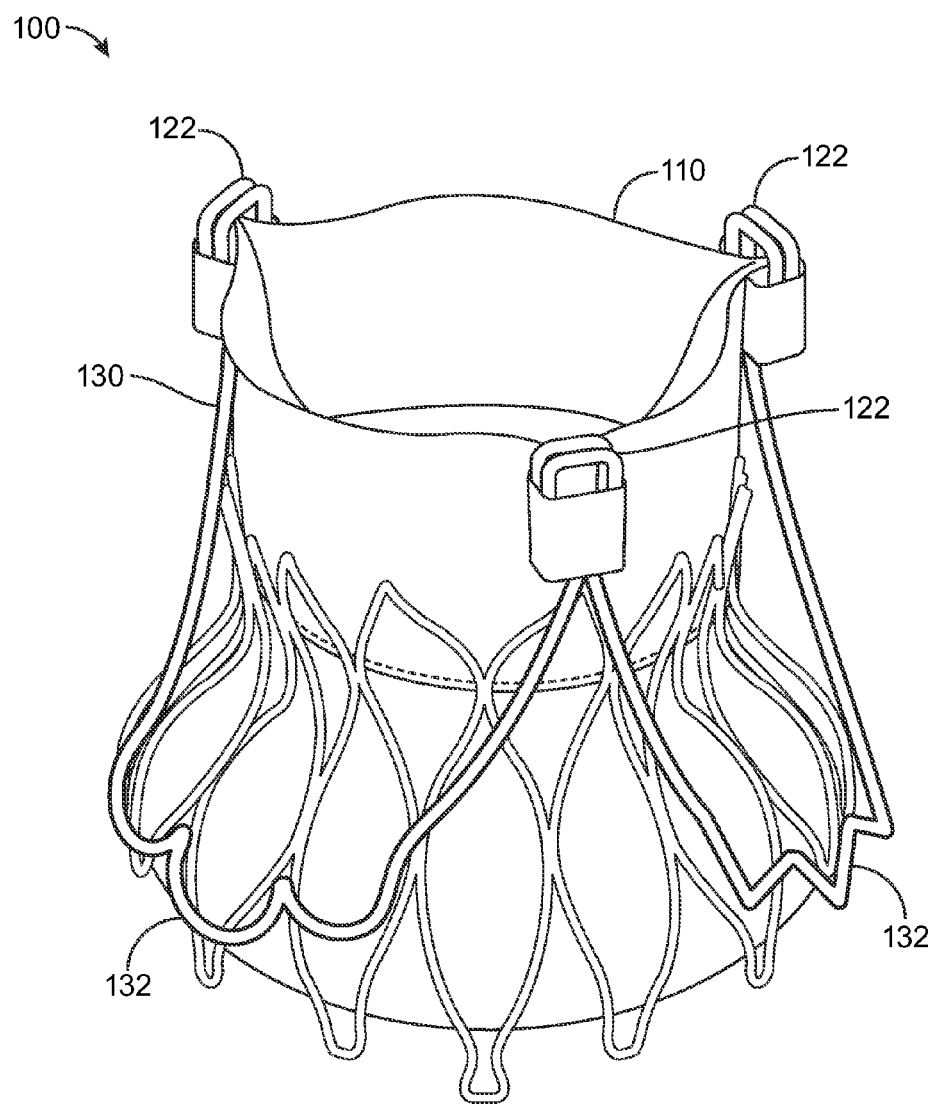

In some embodiments, as illustrated in FIG. 8, the control arms 130 may include different positional markers 132 to readily identify each control arm 130 from another control arm 130. In some embodiments the control arms 130 may include multiple bends as shown in FIG. 8. In some embodiments the control arms 130 may include multiple straight portions. In some embodiments multiple types or forms of positional markers 132 can be used.

Figure 9:
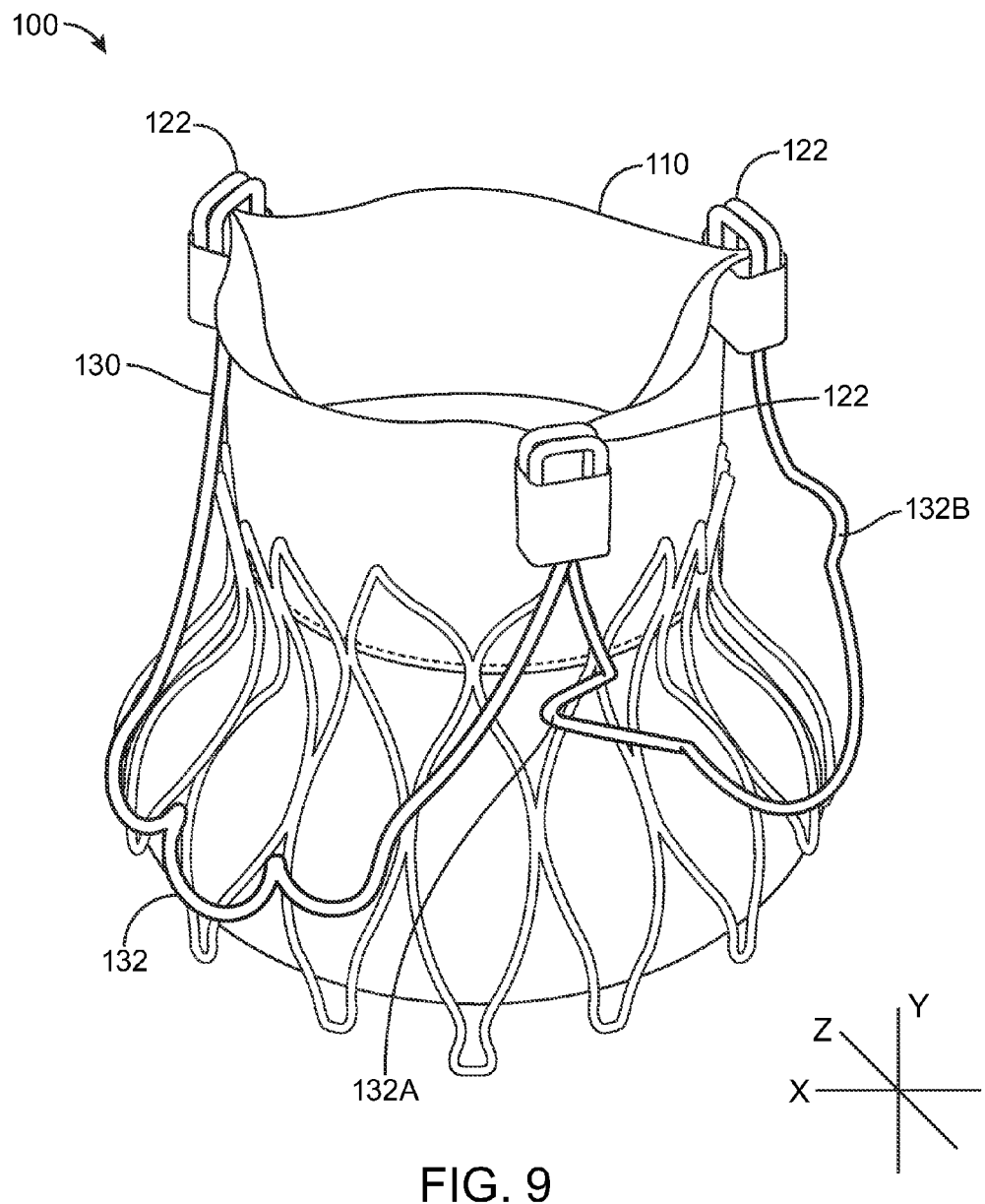

In some embodiments, as shown in FIG. 9, this bend or positional marker 132A may be toward the frame 120 in the z-direction. In some embodiments, this bend or positional marker 132B may be away from the frame 120 in the z-direction.

In some embodiments a different positional marker 132 can be used on each control arm. For example in a prosthetic heart valve 100 comprising three control arms 130, each control arm 130 may have a different type of positional marker 132. A first control arm 130 can have a bends to serve as positional marker 132. A second control arm can have a character to serve as positional marker 132. A third control arm 130 may include a geometric shape to serve as positional marker 132.

In some embodiments similar types of positional markers 132 may be used on multiple control arms 130 or different embodiments of the positional marker 132 may be used. For example on a prosthetic heart valve 100 including three control arms 130, one control arm 130 may have a "C" to serve as a positional marker, one control arm 130 may have a "D" to serve as a positional marker, and one control arm 130 may have a "E" to serve as a positional marker.

In some embodiments that include multiple control arms 130, each control arm 130 make may include a differently shaped positional marker 132. In some embodiments with three control arms 130 one control arm 130 may include a positional marker 132 shaped like a rectangle, one control arm 130 could include a positional marker 132 shaped like a triangle, and one control arm 130 could include a positional marker 132 shaped like an oval.

Figure 10:
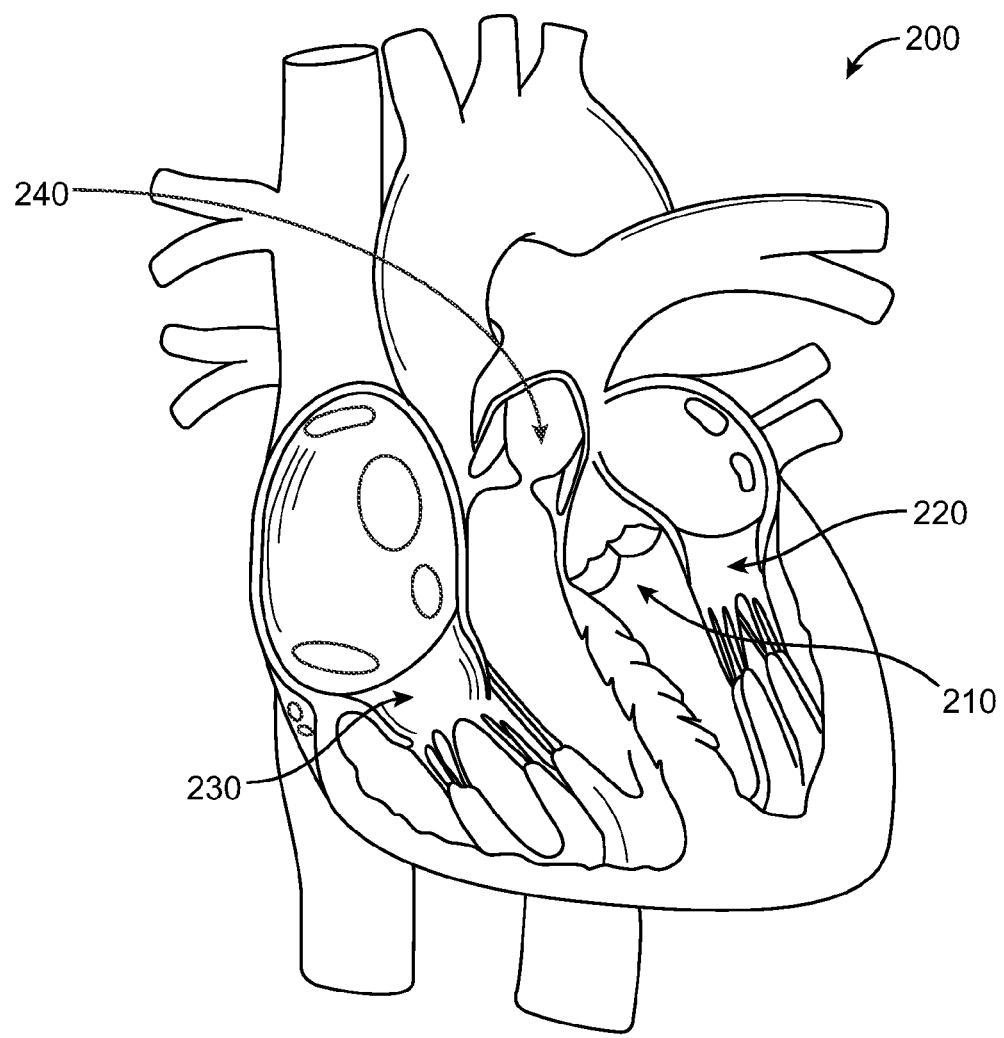

FIG. 10 illustrates a subject's heart 200, which contains four native heart valves. Native heart valves include an aortic native heart valve 210, mitral valve 220, tricuspid valve 230, and pulmonary valve 240. In some embodiments the prosthetic heart valve 100 may be positioned within a subject's heart 200. The prosthetic heart valve 100 may be positioned proximate any native heart valve, including the aortic valve, mitral valve, tricuspid valve, or pulmonary valve. In addition any discussion of a prosthetic heart valve 100 being positioned proximate one type of native valve, such as an aortic native heart valve 210 should be understood as contemplating the same or a similar prosthetic heart valve 100 being implanted in any other type of heart valve, such as a mitral valve 220, tricuspid valve 230, or pulmonary valve 240.

Figure 11:
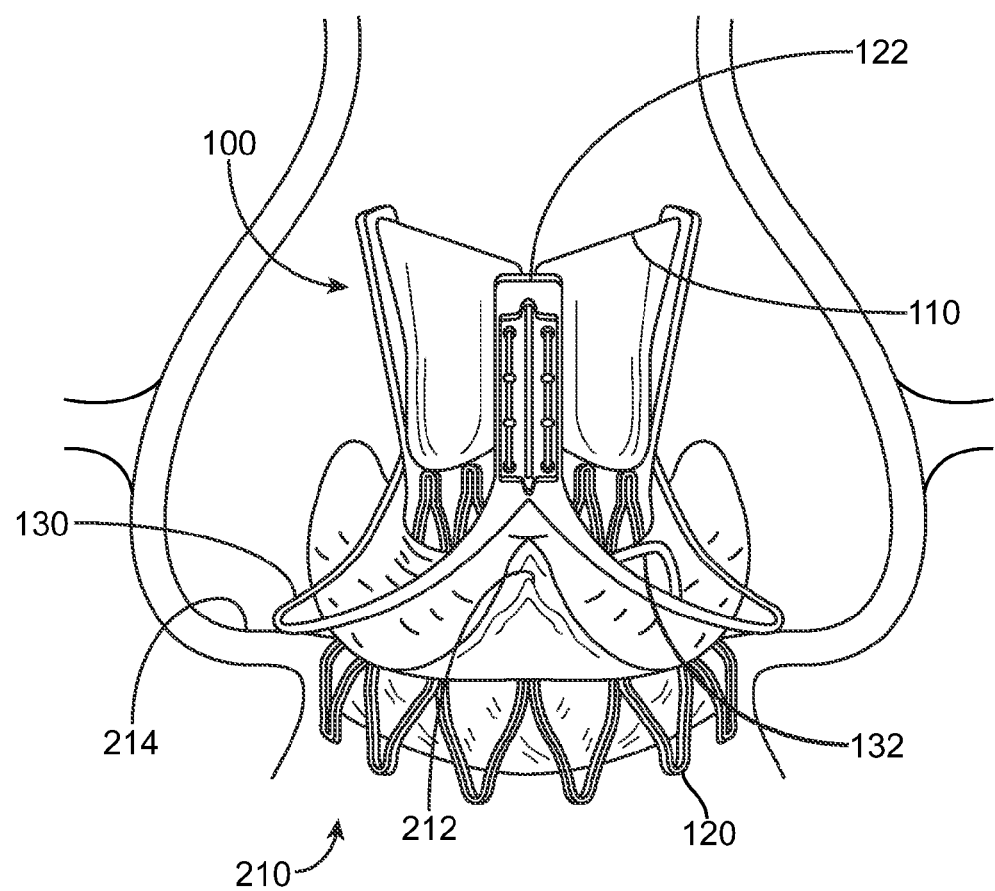
FIG. 11 illustrates a subject's heart in accordance with some embodiments.

FIG. 11 illustrates a prosthetic heart valve 100 in situ after completion of the implantation procedure, in accordance with some embodiments of the present invention. In this embodiment, commissural posts 122 are positioned above respective native commissures 212, without impacting the native commissures 212 (i.e., touching or pushing the commissures). In other words, there may be space between each of commissural posts 122 and its respective native commissure 212.

Control arms 130 (also sometimes described as engagement arms) having a positional marker 132 are positioned within native sinuses 214, such that the ends of the control arms 130 touch the floors of the native sinuses 214. The positional marker 132 shown in this figure is only exemplary, and any other positional marker may be used. In this embodiment, the number of control arms 130 is typically equal to the number of native sinuses 214 of the native valve, and the control arms 130 are radially separated by approximately equal angles. The three-dimensional shape of control arms 130 causes the ends of the control arms 130 to find the lowest point of reach within the floors of the native sinuses 214, thereby enabling self-alignment of prosthetic heart valve 100 proximate the native heart valve 210 and native commissures 212.

As illustrated by FIG. 11, the prosthetic heart valve 100 with corresponding control arm 130 and positional marker 132 may be configured to be positioned proximate an aortic native heart valve 210. As one of skill in the art would appreciate a prosthetic heart valve 100 configured to be positioned proximate an aortic native heart valve 210 may have similar characteristics to a prosthetic heart valve 100 configured to be positioned in a pulmonary valve 240. Some similar characteristics may include orientation or structure of the prosthetic heart valve 100, upstream and downstream orientation of the prosthetic heart valve 100, and others.

In typical human subjects, the native heart valve 210 has three native commissures 212, which define respective commissural high points, and three respective sinus low points. Prosthetic heart valve 100 is configured to match these high and low points. Such matching enables axial anchoring, without forced bending, crimping, or folding over of the leaflets, and without impinging on the commissures. In this way, prosthetic heart valve 100 embraces the leaflets, rather than squeezing them.

For some applications, control arms 130 are generally aligned with the native leaflets, thereby avoiding local deformation, and distributing force over a larger contiguous area of the leaflet surface.

Figure 12:
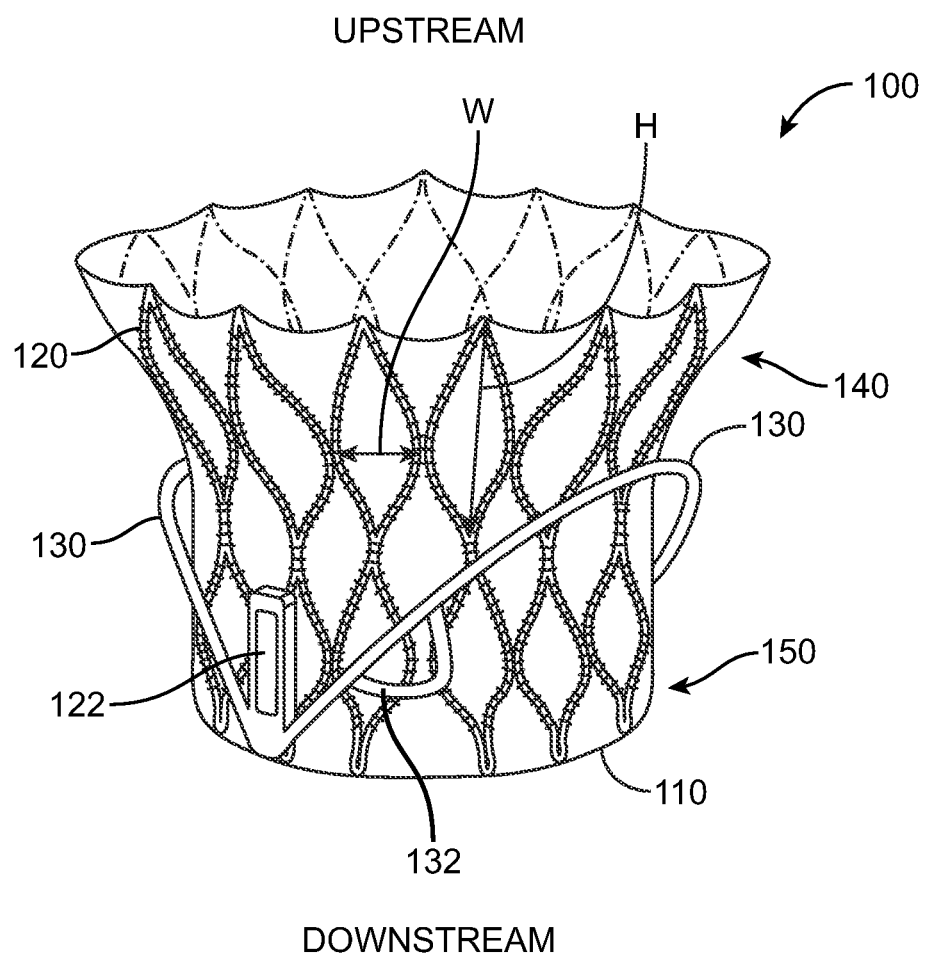
FIGS. 12 and 13 illustrate a prosthetic heart valve being positioned relative to a native heart valve in accordance with some embodiments.

In some embodiments the prosthetic heart valve 100 is configured to be positioned proximate a native mitral valve 220, as illustrated in FIG. 12. In some embodiments prosthetic heart valve 100 that includes control arm 130 and positional marker 132 is similar to the prosthetic heart valve 100 discussed above, to be positioned proximate aortic native heart valve 210. In some embodiments the prosthetic heart valve 100 may include a valve assembly 110 which is oriented opposite that used in procedures involving an aortic native heart valve 210. As FIG. 12 illustrates, the upstream side of prosthetic heart valve 100 may be the end of the frame configured to expand to a larger cross-sectional area. The downstream side of prosthetic heart valve 100 may be the end of the frame configured to expand to a smaller cross-sectional area.

Figure 13:
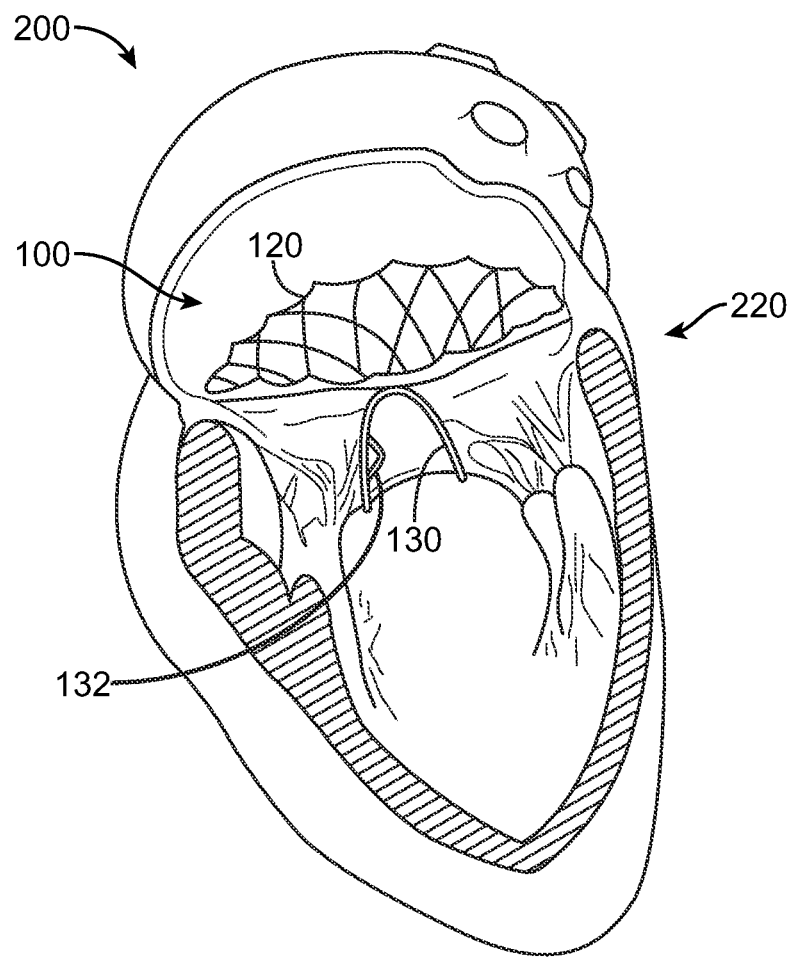

FIG. 13 illustrates a prosthetic heart valve positioned proximate the mitral valve 220. In this orientation the prosthetic heart valve 100 and associated control arms 130 with positional marker 132 may hold without squeezing leaflets of mitral valve 220. In some embodiments the upstream section of prosthetic heart valve 100 is released from the delivery device and is expanded to press against the interior wall of native mitral valve 220. In other embodiments the upstream section is configured to prevent the prosthetic heart valve 100 from migrating.

As illustrated by FIG. 13, the prosthetic heart valve 100 with corresponding control arm 130 and positional marker 132 may be configured to be positioned proximate a mitral valve 220. As one of skill in the art would appreciate a prosthetic heart valve 100 configured to be positioned proximate a mitral valve 220 may have similar characteristics to a prosthetic heart valve 100 configured to be positioned in a tricuspid valve 230. Some similar characteristics may include orientation or structure of the prosthetic heart valve 100, upstream and downstream orientation of the prosthetic heart valve 100, and others.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A prosthetic heart valve comprising:
a valve assembly;
an expandable annular frame coupled to the valve assembly, the frame configured to expand within a native valve annulus, the frame including at least three commissural posts, each commissural post being arranged around a central longitudinal axis of the prosthetic heart valve and being configured to align with a native commissure of a native heart valve; and
at least three control arms disposed circumferentially about the frame when the frame is in an expanded configuration, each control arm extending between a pair of commissural posts of the at least three commissural posts with a first end attached to one commissural post of the pair of commissural posts and a second end attached to the other commissural post of the pair of commissural posts, each control arm configured to hold a native valve leaflet, wherein each control arm extends radially outward from the frame between the pair of commissural posts,
wherein one of the at least three control arms is an asymmetric control arm that forms an asymmetric shape between the first and second ends thereof and the asymmetric shape of the asymmetric control arm between the pair of commissural posts is asymmetric relative to the central longitudinal axis of the frame and
wherein a positional marker is positioned on the asymmetric control arm between the pair of commissural posts, the positional marker positioned on the asymmetric control arm closer to one commissural post of the pair of commissural posts than to the other commissural post of the pair of commissural posts, and
wherein the asymmetric shape of the asymmetric control arm differs from a shape of all other control arms of the at least three control arms of the prosthetic heart valve.

2. The prosthetic heart valve of claim 1, wherein the positional marker comprises a geometric shape.

3. The prosthetic heart valve of claim 1, wherein the positional marker comprises a letter.

4. The prosthetic heart valve of claim 1, wherein the positional marker comprises an asymmetric letter.

5. The prosthetic heart valve of claim 1, wherein the positional marker comprises an asymmetric shape.

6. The prosthetic heart valve of claim 1, wherein the frame comprises a first material with a first radiopacity, and wherein the positional marker comprises a second material with a second radiopacity.

7. The prosthetic heart valve of claim 1, wherein the at least three commissural posts comprise a first material with a first radiopacity, and wherein the positional marker comprises a second material with a second radiopacity.

8. The prosthetic heart valve of claim 1, comprising the positional marker welded to the control arm.

9. The prosthetic heart valve of claim 1, wherein the asymmetric control arm comprises one or more bends closer to one commissural post of the pair of commissural posts than to the other commissural post of the pair of commissural posts.

10. The prosthetic heart valve of claim 1, wherein the positional marker comprises multiple bends in the asymmetric control arm.

11. The prosthetic heart valve of claim 1, wherein the positional marker is a bend oriented toward the frame.

12. The prosthetic heart valve of claim 1, wherein the positional marker is a bend oriented away from the frame.

13. A prosthetic heart valve comprising:
a valve assembly;
an expandable annular frame coupled to the valve assembly, the frame configured to expand within a native valve annulus, the frame including at least three commissural posts, each commissural post being arranged around a central longitudinal axis of the prosthetic heart valve and being configured to align with a native commissure of a native heart valve; and
at least three control arms disposed circumferentially about the frame when the frame is in an expanded configuration, each control arm extending between a pair of commissural posts of the at least three commissural posts with a first end attached to one commissural post of the pair of commissural posts and a second end attached to the other commissural post of the pair of commissural posts, each control arm configured to hold a native valve leaflet, wherein each control arm extends radially outward from the frame between the pair of commissural posts,
wherein one of the at least three control arms is an asymmetric control arm extending radially outward from the frame between the pair of commissural posts, and
wherein the assymmetric control arm forms an asymmetric shape between the pair of commissural posts relative to the central longitudinal axis of the frame, and
wherein the asymmetric shape comprises one or more bends in the asymmetric control arm positioned closer to one commissural post of the pair of commissural posts than to the other commissural post of the pair of commissural posts, and
wherein the asymmetric shape of the asymmetric control arm differs from a shape of all other control arms of the at least three control arms of the prosthetic heart valve.

14. A prosthetic heart valve comprising:
a valve assembly; and
an expandable annular frame coupled to the valve assembly, the frame configured to expand within a native valve annulus, the frame including exactly three commissural posts including a first commissural post, a second commissural post, and a third commissural post, wherein each commissural post is arranged around a central longitudinal axis of the prosthetic heart valve and is configured to align with a native commissure of a native heart valve; and
exactly three control arms disposed circumferentially about the frame when the frame is in an expanded configuration including a first control arm, a second control arm, and a third control arm, each control arm configured to hold a native valve leaflet,
wherein the first control arm extends between the first and second commissural posts with a first end attached to the first commissural post and a second end attached to the second commissural post, the first control arm extending radially outward from the frame between the first and second commissural posts, and wherein the second control arm extends between the second and third commissural posts with a first end attached to the second commissural post and a second end attached to the third commissural post, the second control arm extending radially outward from the frame between the second and third commissural posts, and wherein the third control arm extends between the third and first commissural posts with a first end attached to the third commissural post and a second end attached to the first commissural post, the third control arm extending radially outward from the frame between the third and first commissural posts, and wherein at least the first control arm is an asymmetric control arm that forms an asymmetric shape between the first and second ends thereof and the asymmetric shape of the asymmetric control arm between the first and second commissural posts is asymmetric relative to the central longitudinal axis of the frame, and wherein a positional marker is positioned on the first control arm, the positional marker positioned on the first control arm closer to the first commissural post than to the second commissural post, and wherein the asymmetric shape of the first control arm differs from a shape of the second control arm and from a shape of the third control arm of the prosthetic heart valve.

15. The prosthetic heart valve of claim 14, wherein the positional marker comprises an asymmetric letter.

16. The prosthetic heart valve of claim 14, wherein the first, second, and third commissural posts comprise a first material with a first radiopacity, and wherein the positional marker comprises a second material with a second radiopacity.

17. The prosthetic heart valve of claim 14, wherein the positional marker is a bend oriented toward the frame.

18. The prosthetic heart valve of claim 14, wherein the positional marker is a bend oriented away from the frame.

19. The prosthetic heart valve of claim 14, wherein at least one of the shape of the second control arm or the shape of the third control arm forms an asymmetric shape between the first and second ends thereof.

20. The prosthetic heart valve of claim 19, wherein the shape of the second control arm differs from the shape of the third control arm.

\* \* \* \* \*